United States Patent [19]
Shafer

[11] Patent Number: 5,336,814
[45] Date of Patent: Aug. 9, 1994

[54] METHOD FOR RECOVERING BIS HYDROXY AROMATIC ORGANIC VALUES AND BIS ARYL CARBONATE VALUES FROM SCRAP AROMATIC POLYCARBONATE

[75] Inventor: Sheldon J. Shafer, Clifton Park, N.Y.

[73] Assignee: General Electric Company, Schenectady, N.Y.

[21] Appl. No.: 116,631

[22] Filed: Sep. 7, 1993

[51] Int. Cl.$^5$ .................. C07C 37/70; C07C 37/74
[52] U.S. Cl. ........................... 568/753; 568/724; 568/749; 558/260; 558/265; 558/268
[58] Field of Search ............... 568/753, 749, 724; 558/260, 268, 265

[56] References Cited
U.S. PATENT DOCUMENTS

| | | |
|---|---|---|
| 2,791,616 | 5/1957 | Luten, Jr. .................. 568/724 |
| 4,121,774 | 10/1978 | van der Lely et al. .............. 239/664 |
| 4,212,774 | 7/1980 | Oota .................................. 210/321 |
| 4,478,510 | 3/1986 | Doerr ................................ 541/485 |
| 4,605,762 | 8/1986 | Mandoki .......................... 541/485 |
| 4,885,407 | 12/1989 | Fox et al. ......................... 568/724 |
| 5,045,122 | 9/1991 | Tindall et al. .................... 560/719 |

Primary Examiner—Werren B. Lone
Attorney, Agent, or Firm—William A. Teoli; William H. Pittman

[57] ABSTRACT

A method is provided for depolymerizing scrap aromatic polycarbonate to salvage component monomers by initially effecting aromatic polycarbonate depolymerization by basic phenolysis to produce a mixture having dihydric phenol, and diarylcarbonate. Recovery of the dihydric phenol is effected by distillation of a crystalline dihydric phenol/phenol adduct. Diarylcarbonate is recovered by distillation of the resulting mother liquor after carboxylic acid treatment.

6 Claims, 1 Drawing Sheet

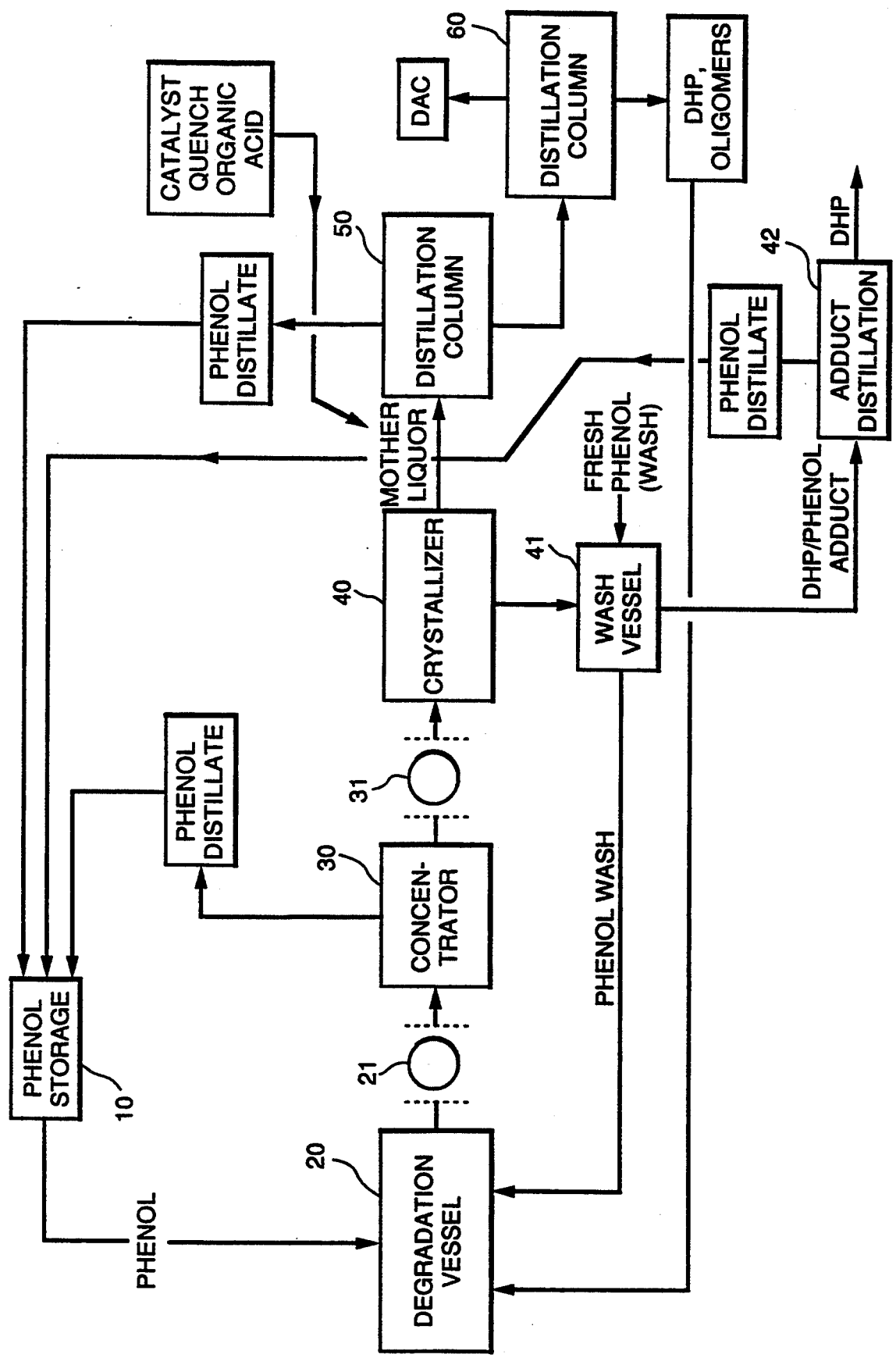

METHOD FOR RECOVERING BIS HYDROXY AROMATIC ORGANIC VALUES AND BIS ARYL CARBONATE VALUES FROM SCRAP AROMATIC POLYCARBONATE

BACKGROUND OF THE INVENTION

The present invention relates to a method for recovering component aromatic polycarbonate values, such as dihydric phenol and diarylcarbonate from scrap aromatic polycarbonate. The scrap aromatic polycarbonate is initially subjected to basic phenolysis. Dihydric phenol is then recovered as a dihydric phenol/phenol adduct, and diarylcarbonate is recovered by distillation of the resulting mother liquor.

Prior to the present invention as shown by Idel, U.S. Pat. No. 4,212,774, scrap polycarbonate was saponified in bulk in the presence of an aqueous alkali metal hydroxide solution to produce bisphenol A. The resulting mixture was thereafter phosgenated to produce a polycarbonate. Although polycarbonate made by Idel exhibited valuable mechanical and rheological properties, the product was often contaminated with organic additives which were not eliminated during the saponification and phosgenation stages. As a result, the physical properties of the recycled polycarbonate were often sub-standard. It would be desirable, therefore, to be able to depolymerize scrap polycarbonate to allow for the recovery of basic polymer forming ingredients, such as readily purifiable bisphenol A and diphenylcarbonate. These basic ingredients can be converted to polycarbonate by standard melt-transesterification procedures; the resulting polycarbonate has substantially the same physical properties as virgin polycarbonate source material.

SUMMARY OF THE INVENTION

The present invention is based on the discovery that polycarbonate scrap can be salvaged by initially depolymerizing the polymer through basic phenolysis. The scrap can be heated in the presence of a major amount of phenol and an effective amount of a basic catalyst. A mixture is formed comprising phenol, dihydric phenol, diphenylcarbonate, and polycarbonate oligomers. If desired, the mixture can be filtered at this stage, to free it of contaminants including pigments, fillers, and polymeric degradation products. The mixture can then be concentrated by effecting the separation of excess phenol to provide for the production and separation of a dihydric phenol/phenol adduct which can be collected as a crystalline solid at an appropriate mixture viscosity. Recovery of the dihydric phenol from the adduct can be readily achieved by phenol distillation.

The mother liquor remaining after separation of the dihydric phenol/phenol adduct from the depolymerization mixture can then be treated with an effective amount by weight of an organic carboxylic acid based on the weight of mixture. Distillation of the mother liquor has been found to effect the initial separation of phenol followed by diarylcarbonate. The still bottoms containing polycarbonate oligomers can be recycled to the basic phenolysis stage. Basic polycarbonate monomers in the form of dihydric phenol and diarylcarbonate are thus provided which can be readily purified and recycled to provide the production of virgin polycarbonate.

STATEMENT OF THE INVENTION

There is provided by the present invention, a method for recovering dihydric phenol and diarylcarbonate values from scrap aromatic polycarbonate comprising carbonate repeat units having the formula,

  (1)

where R is a C(6-30) divalent aromatic organic group, which method comprises, (1) heating the scrap aromatic polycarbonate at a temperature in the range of about 60° C. to about 250° C. in the presence of 3 to 50 moles of a monohydric phenol having the formula, $$R^1OH, \quad (2)$$

per mole of the carbonate repeat unit and an effective amount of a basic depolymerization catalyst to produce a mixture comprising the monohydric phenol, dihydric phenol having the formula, $$HOROH, \text{ and} \quad (3)$$

diarylcarbonate having the formula,

  (4)

where $R^1$ is a $C_{(6-13)}$ monovalent organic radical, (2) distilling monohydric phenol from the resulting mixture of (1), or in the event the scrap aromatic polycarbonate contains insoluble polycarbonate contaminants, initially filtering the insoluble contaminants from the mixture, where the distillation of monohydric phenol from the mixture is continued until a concentration of about 10% to about 35% of dihydric phenol is achieved, based on total weight of the resulting mixture, (3) separating dihydric phenol/monohydric phenol adduct from the resulting mixture of (2) at a temperature of about 40° C. to about 80° C., (4) vacuum distilling monohydric phenol from the resulting mother liquor of the mixture of (3) in the presence of an effective amount of an organic acid, and (5) vacuum distilling diarylcarbonate from the residue from the mixture of (4).

There are included within the dihydric phenol of formula (3) compounds, such as 2,2-bis- (2-hydroxyphenyl)propane, 2,4'-dihydroxy-biphenylmethane, bis-2(2-hydroxyphenyl)methane, 2,2-bis- (4-hydroxyphenyl)propane, referred to hereinafter as "bisphenol A" or "BPA", 1,1-bis (4-hydroxyphenyl)ethane, 1,1-bis (4-hydroxyphenyl) propane, 4,4'-dihydroxybiphenyl, 4,4'-dihydroxy-3,3', 5,5'-tetramethylbiphenyl, 2,4-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenyl-sulfide, tetramethyl bisphenol,1, 1,1-dichloro-2, 2-bis(4-hydroxyphenyl) ethylene, 6, 6'-dihydroxy-3,3,3',3'-tetramethyl-bis-,1,1'spiroindane, oxydiphenol, 4,4'-[1,4-phenylenebisoxy]bisphenol,

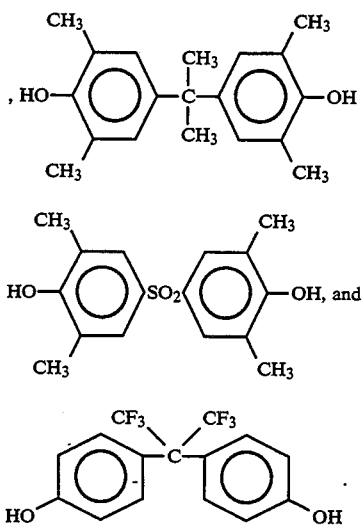

Among the monohydric phenol of formula (2) there are included

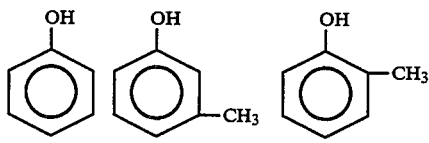

Some of the organic acids which can be used in the practice of the method of the present invention during the recovery of the diarylcarbonate from the dihydric phenol/monohydric phenol adduct mother liquor are, for example, salicylic acid, citric acid, phthalic acid and glutaric acid. Salicylic acid is preferred.

An effective amount of organic acid is from 0.001% to 1.0% by weight of organic acid based on the weight of the adduct mother liquor.

Some of the oligomers which can be recovered as bottoms product after the dihydric phenol/monohydro phenol adduct mother liquor has been heated under reduced pressure to effect the removal of phenol and diarylcarbonate are products having the following formulas, referred to hereinafter as oligomers I, II, III, and IV respectively:

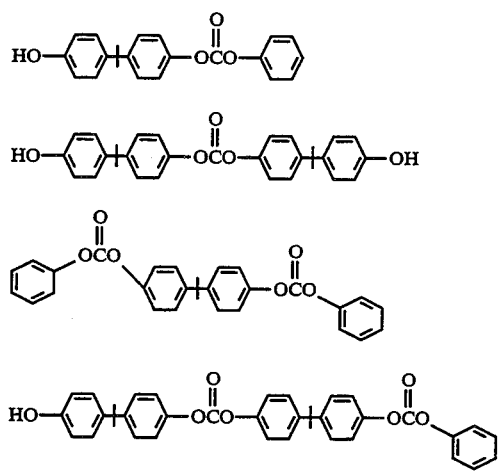

BRIEF DESCRIPTION OF THE DRAWINGS

There is shown in the drawing, a schematic view of a recovery system for salvaging diarylcarbonate (DAC) and dihydric phenol (DHP) from scrap aromatic polycarbonate. A degradation vessel is shown to effect the depolymerization of the aromatic polycarbonate followed by a concentrator to effect the selective removal of the phenol. A crystallizer is shown to provide the formation of a dihydric phenol/monohydric phenol adduct. The adduct is separated, washed and distilled to provide recovery of dihydric phenol. The mother liquor from the crystallizer is treated with an organic acid to neutralize residual basic species. Distillation of the treated mother liquor provides recovery of diarylcarbonate.

More particularly, there is shown at 10 means for phenol storage to provide a phenol source in the degradation vessel at 20 during the depolymerization of scrap aromatic polycarbonate in the presence of a effective amount of the depolymerization catalyst. The depolymerization catalyst can be a basic material, which preferably has a boiling point in the range of 140° C.–200° C. Suitable materials are $C_{(2-20)}$ trialkyl amine, for example tripropyl amine. A $C_{(2-20)}$ quaternary ammonium hydroxide, eg, tetrabutylammonium hydroxide also can be used. An effective amount of the basic depolymerization catalyst is 0.001% to 0.5% by weight, and preferably 0.01% to 0.05% by weight, based on the weight of depolymerization mixture. Filtration of the alepolymerization mixture optionally can be effected at 21 before it is fed into the concentrator at 30 or after the concentrator at 31.

The solids concentration can be raised by effecting the removal of the monohydric phenol through distillation. When the dihydric phenol is at a desirable concentration in the depolymerization mixture, such as at about 10% to 35% by weight, the temperature of the mixture can be lowered to a range of from about 40° C. to 80° C. to facilitate the formation of the dihydric phenol/monohydric phenol adduct. Separation of the adduct can be achieved by filtration, or other means, where such factors as the viscosity of the mixture, ease of filtration, and the level of the dihydric phenol in the form of the adduct are considered. The dihydric phenol/monohydric phenol adduct can be washed in the wash vessel with monohydric phenol at 41 and then distilled at 42 to provide for the recovery of the dihydric phenol. Preferably, the dihydric phenol is bisphenol-A. An effective amount of an organic carboxylic acid can be added to the depolymerization mother liquor after separation of the dihydric phenol/monohydric phenol adduct. After the basic depolymerization catalyst has been neutralized, the mother liquor can then be distilled as shown at 50 and 60 to provide for the recovery of the diarylcarbonate, such as diphenylcarbonate. The residue or distillation bottoms that remain in the mixture are generally dihydric phenol and oligomers as shown above.

In order that those skilled in the art will be able to practice the present invention the following examples are given by way of illustration not by way of limitation. All parts are by weight unless otherwise indicated.

EXAMPLE 1

A mixture of 263.4 grams of phenol (2.80 moles) and 35.6 grams of a polycarbonate resin, Lexan 141 polycarbonate, a product of GE Plastics Division, (0.140 moles)

was heated at a temperature of 160° C. under a nitrogen atmosphere. After 10 minutes, the mixture was agitated; after 15 minutes, all of the polycarbonate had dissolved. There was added to the mixture, 0.060 grams tripropyl amine (0.42 mmoles); the mixture was then stirred for one hour and forty minutes. The temperature of the mixture was raised to 180° C. and held there for fifteen minutes. A titer was removed from the mixture for analysis. It consisted of about 79% by weight of phenol, 8.2% by weight of bisphenol-A, 7.8% by weight of diphenylcarbonate, 3.5% by weight of oligomer 1, 0.2% by weight oligomer 2, and the balance traces of oligomer 3 and oligomer 4 which are previously defined.

Vacuum was applied to the system to effect a rapid distillation of phenol. There was obtained 108.6 grams of material consisting of 99% phenol. The residue consisted of about 68.1% by weight phenol, 12.8% by weight of bisphenol-A, 12.3% by weight of diphenylcarbonate, and the balance of the mixture was the above-shown oligomers. The mixture was then allowed to cool and maintained at a temperature of 50-52° C. for a period of about one hour. A few seed crystals of bisphenol-A/phenol adduct were added and within a few minutes crystals began to form. After about twelve hours, the mixture was poured into a Buchner funnel to recover a crystalline solid. There was obtained 23.8 grams of crude bisphenol-A/phenol adduct. Samples of the adduct mother liquor removed by HPLC showed 70.5% by weight phenol, 7.6% by weight of bisphenol-A, 13.4% of diphenylcarbonate, and the balance oligomers. There was obtained an overall yield of about 35% by weight of bisphenol-A.

There was added 95.3 milligrams of salicylic acid (0.69 mmoles) to 151.5 grams of the mother liquor remaining after the separation of the bisphenol-A/phenol adduct. The mixture was heated to 120° C. along with agitation under reduced pressure to effect phenol distillation. The initial 94.4 grams of material collected over a period of 15-20 minutes showed by HPLC, 93.9% phenol, 1.1% bisphenol-A, and 1.9% diphenyl carbonate and about 1% oligomer.

The residue of the depolymerization mother liquor was then heated to 210° C. under a nitrogen atmosphere for 10 minutes and then subjected to reduced pressure. There was obtained 34.1 grams of distillate. Analysis by HPLC showed 49.5% of phenol, 3.9% by weight of bisphenol-A, and 43.2% by weight of diphenylcarbonate. The remaining 1-2.2% was oligomer. Additional diphenylcarbonate was obtained in the still head to provide an overall yield of diphenylcarbonate recovery of 17.5 grams or 67%.

EXAMPLE 2

The procedure of Example 1 was repeated except that a mixture of clear and opaque polycarbonate pellets was processed. After depolymerization, the initial titer showed 78.8% by weight phenol, 7.9% by weight of bisphenol-A, 8.2% by weight of diphenylcarbonate, 3.8% by weight of oligomer 1, 0.2% by weight of oligomer 2, 0.3% by weight of oligomer 3, and 0.1% by weight of oligomer 4. The depolymerization mixture was then subjected to reduced pressure for 12-15 minutes. There was obtained 147.3 grams of condensate which consisted of about 99% phenol. Based on HPLC, the residue in the depolymerization mixture consisted of 57.8% by weight phenol, 16.3% by weight of bisphenol-A, 16.1% by weight of diphenylcarbonate, 7.2% by weight of oligomer 1, 0.6% by weight of oligomer 2, 0.7% by weight of oligomer 3, and 0.3% by weight of oligomer 4.

The residual was then passed through a medium frit (ASTM 10-15) glass funnel to remove traces of insolubles, such as filler and pigment. The remaining filtrate weighed 139.2 grams. The remaining filtrate (138 grams) was agitated at a temperature of between 50-51° C. for a period of about 10 minutes, at which time crystals began forming. After crystal formation, the mixture was held for three and one-half hours at 50-51° C. The mixture was then filtered with a Buchner funnel under vacuum. There was obtained, 29.8 grams of solid and 96.2 grams of mother liquor. HPLC analysis of the mother liquor showed 62.2% by weight phenol, 7.3% by weight of bisphenol-A, 18.9% by weight of diphenylcarbonate and the balance oligomers.

There was added 0.0917 grams of salicylic acid (0.66 moles) to 96.2 grams of the mother liquor. The mixture was then heated for 10 minutes at 120° C. and subjected to vacuum to effect a rapid distillation of phenol. Based on procedures shown in Example 1, there was obtained an overall yield of 45% by weight bisphenol-A and 72% by weight of diphenylcarbonate.

Although the above examples are directed to only a few of the very many variables which can be used in the practice of the method of the present invention, it should be understood that the method of the present invention involves the use of a much broader variety of the reagents and conditions as setforth in the description proceeding these examples.

What is claimed is:

1. A method for recovering dihydric phenol and diarylcarbonate values from scrap aromatic polycarbonate comprising carbonate repeat units having the formula,

where R is a $C_{(6-30)}$ divalent aromatic organic group, which method comprises,
(1) heating the scrap aromatic polycarbonate at a temperature in the range of about 60° C. to about 250° C. in the presence of about 3 to about 50 moles of a monohydric phenol having the formula,

per mole of the carbonate repeat unit and an effective amount of a basic depolymerization catalyst to produce a mixture comprising the monohydric phenol, dihydric phenol having the formula,

diarylcarbonate having the formula,

where $R^1$ is a $C_{(6-13)}$ monovalent organic radical,
(2) distilling monohydric phenol from the resulting mixture of (1), or in the event the scrap aromatic polycarbonate contains insoluble polycarbonate contaminants, initially filtering the insoluble contaminants from the mixture, where the distillation of monohydric phenol from the mixture is continued until a concentration of about 10% to about 35% of dihydric phenol is achieved, based on total weight of the resulting mixture, (3) separating dihydric phenol/monohydric phenol adduct from the resulting mixture of (2) at a temperature of about 40° C. to about 80° C., (4) vacuum distilling monohydric phenol from the resulting mother liquor of the mixture of (3) in the presence of an effective amount of an organic acid, and (5) vacuum distilling diarylcarbonate from the residue from the mixture of (4).

2. A method on accordance with claim 1, where the scrap aromatic polycarbonate is scrap bisphenol A polycarbonate.

3. A method on accordance with claim 1, where the diarylcarbonate is diphenylcarbonate.

4. A method on accordance with claim 1, where the organic acid is salicylic acid.

5. A method on accordance with claim 1, where the monohydric phenol is hydroxy benzene.

6. A method in accordance with claim 1, where the dihydric phenol is recovered from the dihydric phenol/monohydric phenol adduct of step 3. WAT/mm

* * * * *